United States Patent [19]
Sakurai et al.

[11] Patent Number: 4,892,676
[45] Date of Patent: Jan. 9, 1990

[54] PHENYL PYRIMIDINE COMPOUND AND LIQUID CRYSTALLINE COMPOSITION

[75] Inventors: Takao Sakurai; Tadahiko Yokota; Eri Komatsu; Naoko Mikami; Ryoichi Higuchi; Koji Takeuchi, all of Kawasaki, Japan

[73] Assignee: Ajinomoto Co., Inc., Tokyo, Japan

[21] Appl. No.: 94,290

[22] Filed: Sep. 8, 1987

[30] Foreign Application Priority Data

Sep. 9, 1986 [JP] Japan ................................ 61-211894
Jan. 9, 1987 [JP] Japan .................................... 62-3048

[51] Int. Cl.$^4$ ........................ G02F 1/13; C09K 19/34; C07D 239/02
[52] U.S. Cl. ........................... 252/299.61; 252/299.01; 252/299.5; 350/350 R; 350/350 S; 544/298; 544/318
[58] Field of Search ........... 252/299.61, 299.5, 299.01; 350/350 R, 350 S; 544/298, 318

[56] References Cited

U.S. PATENT DOCUMENTS

| 4,725,688 | 2/1988 | Taguchi et al. | 252/299.61 |
| 4,820,839 | 4/1989 | Krause et al. | 252/299.61 |
| 4,826,621 | 5/1989 | Terashima et al. | 252/299.61 |
| 4,834,904 | 5/1984 | Krause et al. | 252/299.61 |

FOREIGN PATENT DOCUMENTS

| 206228 | 12/1986 | European Pat. Off. | 252/299.61 |
| 225195 | 6/1987 | European Pat. Off. | 252/299.61 |
| 248335 | 12/1987 | European Pat. Off. | 252/299.61 |
| 2257588 | 9/1973 | Fed. Rep. of Germany | 252/299.61 |
| 3404117 | 8/1985 | Fed. Rep. of Germany | 252/299.61 |
| 3500909 | 7/1986 | Fed. Rep. of Germany | 252/299.61 |
| 3515373 | 11/1986 | Fed. Rep. of Germany | 252/299.61 |
| 3515374 | 11/1986 | Fed. Rep. of Germany | 252/299.61 |
| 240385 | 10/1986 | German Democratic Rep. | 252/299.61 |
| 240386 | 10/1986 | German Democratic Rep. | 252/299.61 |
| 61-215374 | 9/1986 | Japan | 252/299.61 |
| 61-246284 | 11/1986 | Japan | 252/299.61 |
| 62-209190 | 9/1987 | Japan | 252/299.61 |
| 63-37186 | 2/1988 | Japan | 252/299.61 |
| 8600067 | 1/1986 | PCT Int'l Appl. | 252/299.61 |
| 8606401 | 11/1986 | PCT Int'l Appl. | 252/299.61 |

OTHER PUBLICATIONS

Zaschke, H., Advances in Liquid Crystal Research & Applications, Bata, L. ed., Pergamon Press, Oxford, pp. 1059–1074 (1980).

Demus, D. et al., Flussige Kristalle in Tabelleh II, VEB Deutscher Verlag fur Grundstoffindustrie, Leipzig, pp. 375–388 (1984).

Primary Examiner—Teddy S. Gron
Attorney, Agent, or Firm—Oblon, Spivak, McClelland, Maier & Neustadt

[57] ABSTRACT

A phenyl pyrimidine compound of this invention represented by the following formula (I) forms a smectic C phase and is useful for a constituent of a ferroelectric liquid crystal composition.

$$R_1—Ph—Py—R_2 \qquad (I)$$

wherein Ph represents 1,4-phenylene group, Py represents 2,5-pyrimidine, $R_1$ and $R_2$ represent independently an acyloxy group or alkoxy group, either $R_1$ or $R_2$ represents a linear acyloxy group or a linear alkoxy group having more than seven carbon atoms. The compound of this invention has a properties of 1 a low viscosity, 2 of forming a smectic C phase (Sc), 3 of being more than 70° C. of an upper limit temperature of a Sc phase. By applying these properties it is able to give a good alignment effect of a composition comprising the compound using a conventional alignment effect of a TN type cell.

11 Claims, 2 Drawing Sheets

PHENYL PYRIMIDINE COMPOUND AND LIQUID CRYSTALLINE COMPOSITION

BACKGROUND OF THE INVENTION

1. Field of the Invention

The present invention relates to a novel, optically active phenyl pyrimidine compound and a liquid crystal composition comprising the optically active phenyl pyrimidine compound.

In this instant specification, by the term "liquid crystalline substance of material" is meant not only a substance showing a liquid crystalline phase but also a substance or material which is valuable as a constituent of a liquid crystal composition though it is not detected that the substance or material shows a liquid crystalline phase.

2. Description of the Related Art

As the display system using a liquid crystal display element, which is widely utilized in practice at present, there can be mentioned the twisted nematic type (TN type) and dynamic scattering type (DS type). In these display system, display is performed by a nematic liquid crystalline cell comprising a nematic liquid cell as the main component. One defect of the conventional nematic liquid cell is a low response speed, and only a response speed of several milliseconds is obtained. This defect is one cause of limitation of the application range of the nematic liquid cell. Recently, however, it has been found that a high response speed can be obtained if a smectic liquid crystalline cell is used.

It has been clarified that some optically active smectic liquid crystals have a ferroelectric property, and there are great expectation on the utilization of such liquid crystals. Liquid crystals having a ferroelectric property, that is, ferroelectric liquid crystals, are compounds synthesized by R. B. Meyer et al in 1975, which are represented by 2-methylbutyl 4-(4-n-decyloxybenzilydene-amino)cinnamate (hereinafter referred to as "DOBAMBC"). The compounds are characterized as exhibiting a ferroelectric property in the chiral smectic C phase (hereinafter referred to as "Sc * phase") [J. Physique, 36, L-69 (1975)].

N. A. Clark et al found that a high-response speed of an order of microseconds is obtained in a film cell of DOBAMBC [Appl. Phys. Lett., 36, 89 (1980)], and with this finding as a momentum, the ferroelectric crystal has attracted attention as a material applicable not only to a display system such as a liquid crystal television but also to an optical printer head, an optical Fourier converting element, a light valve, and other optoelectronic elements because of high-speed response characteristics.

Since DOBAMBC has a small spontaneous polarization and is a Schiff base, it has poor physical and chemical stabilities. Accordingly, various physically and chemically stable compounds have been investigated as ferroelectric liquid crystalline materials. At present, research work on the development of ferroelectric liquid crystalline materials is concentrated on an enhancement of the high-speed response characteristic, orientation effect, contrast characteristic, memory characteristic, and threshold value characteristic, and optimization of practical properties such as the temperature dependencies of these characteristics.

However, none of the known ferroelectric liquid crystals, when used alone, shows a large spontaneous polarization, a low viscosity, a long helical pitch, an appropriate molecular tilt angle and a continuous phase transition (V*→SA→Sc*) within a broad temperature range including room temperature such that the above-mentioned practically desired properties are manifested. Therefore, practically, attempts have been made to optimize the foregoing characteristics by mixing several compounds such as a compound having or inducing a large spontaneous polarization, a compound having a low viscosity and compounds having reverse helical pitches. The incorporation of a ferroelectric liquid crystal showing a ferroelectric characteristic within a broad temperature range or a smectic C liquid crystal (Sc) which is not chiral is effective for obtaining a liquid crystal composition showing a ferroelectric characteristic within a broad temperature range. A Sc is very important to obtain a liquid crystal composition within a broad temperature range, because a molecular structure of compound formed a Sc phase is a long helical pitch and it is able to comprise the Sc compound without a limitation of a volume in a liquid crystal composition. The research work on the development of a novel compound as a constituent of a liquid crystal composition, which has a performance of a high speed response and shows a Sc phase within a broad temperature range is worth to be carried out.

An optically active phenyl pyrimidine compound represented by following general formula (IV) which has a skeleton to be high speed response has carried out by Seiko Electric Industry Company and Teikoku Kagaku Co., Ltd. (The digest of 11th liquid crystal conference, 2N18, 2N19, 2N20, 2N21)

$R_7$—Ph—Py—$R_8$ (VI)

wherein Ph represents 1,4-phenylene group, Py represents 2,5-pyrimidine group, $R_7$ and $R_8$ represent alkyl group, acyloxy group, alkoxy group or alkylcarbonyloxy group, either $R_7$ or $R_8$ represents an optically active branched group.

One of the defects of the compound is a small spontaneous polarization. But the compound has a good performance of a high speed response because of own low viscosity. Other defect of the compound has not a smectic phase because of having a branched group of the compound. The acknowledge carried out a component technique of a conventional TN type cell is no use on the compound. Further defect of the compound, it is difficult to settle constituent volume in a liquid crystal composition because of an optically active characterisity and an own helical pitch.

On the other hand, a phenyl pyrimidine Sc liquid crystal compound having linear alkyl group represented by following general formula (II) has already known. (H. Zaschke, R. Stolle, Z. Chem. 15, 441 (1975), Flussige Kristalle in Tabellen, Verlag Grundstoffind, Leipzig, 2nd ed. (1976))

Since a phase transition point (SA→Sc) of the compound is low, less than 70° C., the compound is not suitable to use for constituent of a liquid crystal composition.

$R_3$—Ph—Py—$R_4$ (II)

wherein Ph represents 1,4-phenylene group, Py represents 2,5-pyrimidine group, $R_3$ and $R_4$ represent independently linear alkyl group, linear acyloxy group or linear alkoxyl group. Either $R_3$ or $R_4$ represents linear alkyl group having more than seven carbon atoms.

SUMMARY OF THE INVENTION

We investigated a constituent of a ferroelectric liquid crystal composition, as a result we have now completed the present invention based on the novel phenyl pyrimidine compounds.

It is a primary object of the present invention to provide (1) a novel Sc liquid crystal compound or a constituent of a Sc* liquid crystal composition, which is low viscosity, (2) a Sc liquid crystal compound of which an upper limit temperature of a Sc phase is more than 70° C., (3) a liquid crystal compound having a nematic phase, applying a conventional alignment effect of a TN type cell.

In one aspect of the present invention, there is provided a phenyl pyrimidine compound represented by following general formula (I) and a liquid crystal composition comprising the same.

$$R_1-Ph-Py-R_2 \qquad (I)$$

wherein Ph represents 1,4-phenylene group, Py represents 2,5-pyrimidine, $R_1$ and $R_2$ represent independently an acyloxy group or alkoxy group, either $R_1$ or $R_2$ represents a linear acyloxy group or a linear alkoxy group having more than seven carbon atoms.

DESCRIPTION OF THE PREFERRED EMBODIMENTS

Figure 1:
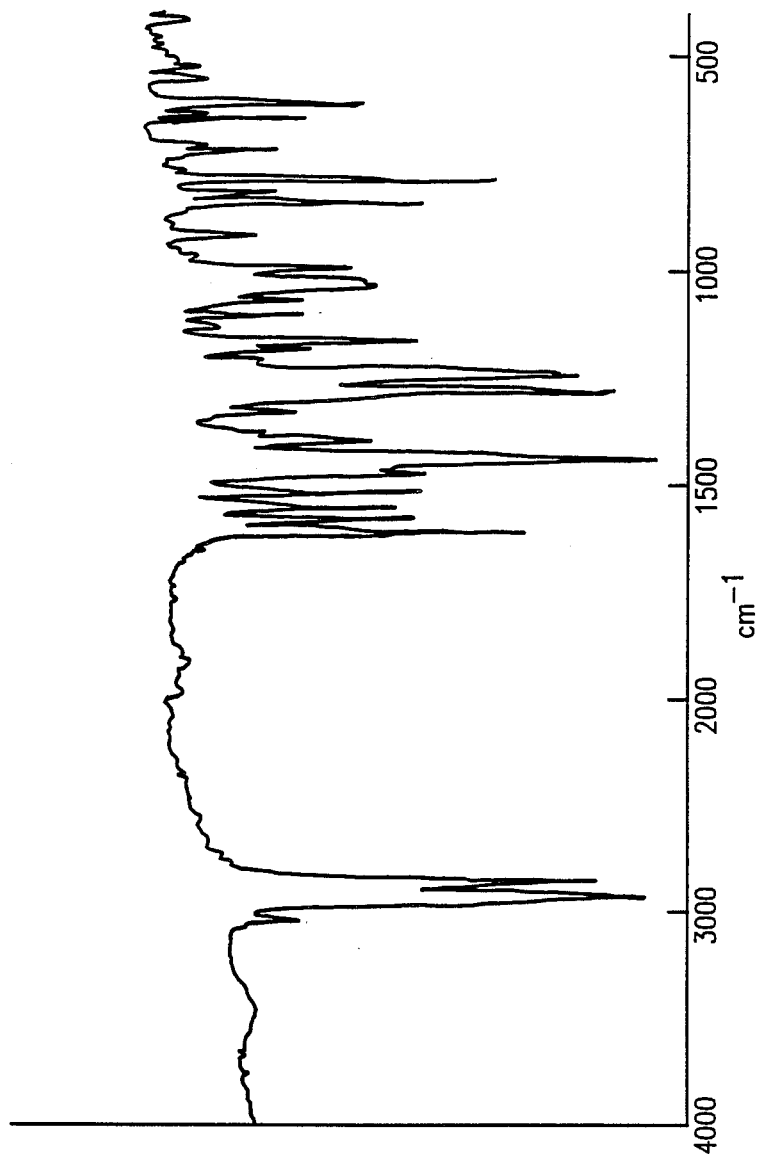
FIG. 1 shows the IR spectrum of the 2-p-octyloxyphenyl-5-octyloxypyrimidine compound obtained in Example 1.
Figure 2:
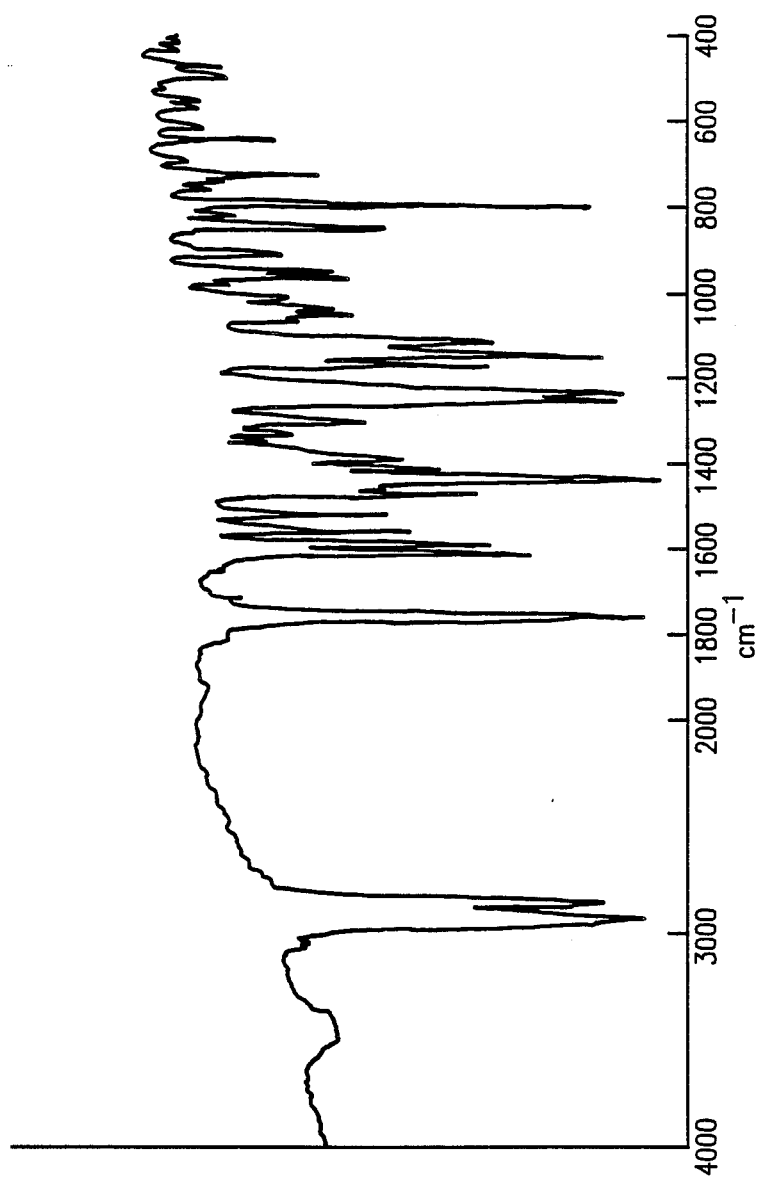
FIG. 2 shows the IR spectrum of the 2-p-octyloxyphenyl-5-octylcarbonyloxypyrimidine compound obtained in Example 2.

A phenyl pyrimidine compound of this invention represented by the following formula (I) forms a smectic C phase and is useful for a constituent of a ferroelectric liquid crystal composition.

$$R_1-Ph-Py-R_2 \qquad (I)$$

wherein Ph represents 1,4-phenylene group, Py represents 2,5-pyrimidine, $R_1$ and $R_2$ represent independently an acyloxy group or alkoxy group, either $R_1$ or $R_2$ represents a linear acyloxy group or a linear alkoxy group having more than seven carbon atoms.

Some of the compounds represented by the above formula (I) of which the seven-fourteen carbon atoms of $R_1$ or $R_2$ group form dependently or independently a smectic C phase. Other compounds represented by the above formula (I) are also important as a constituent of a liquid crystal composition.

The compounds of this invention can be available as a constituent with the compounds of a following two groups;

(1) The compounds disclosed in the following Japan Patent Application Numbers 176823/1983, 175711/1983, 23510/1984, 33511/1984, 74748/1984, 189232/1984, 22920/1985, 87034/1985, 117053/1985, 144136/1985, 162654/1985, 162656/1985, 250335/1985, 272834/1985, 291179/1985.

(2) Compounds having a smectic C phase, such as alkyl alkoxybiphenylcarboxylate, alkyl alkylcarbonyloxybiphenylcarboxylate, alkoxyphenyl alkoxybenzoate, alkyloxycarbonylphenyl alkoxybenzoate, alkoxyalkoxyphenyl alkoxybenzoate, alkoxybiphenyl alkoxybenzoate, alkoxyphenyl alkoxybiphenylcarboxylate, alkoxybiphenyl alkylbenzoate, alkoxyphenyl alkylbiphenylcarboxylate, alkylbiphenyl alkoxybenzoate, alkylphenyl alkoxybiphenylcarboxylate, alkoxybiphenyl alkylcarbonyloxybenzoate, alkoxyphenyl alkylcarbonyloxybiphenylcarboxylate, alkylcarbonyloxy biphenyl alkoxybenzoate, alkylcarbonyloxyphenyl alkoxybiphenylcarboxylate, 5-alkyl-2-(4'-alkoxyphenyl)pyrimidine,
5-alkoxy-2-(4'-alkoxyphenyl)pyrimidine,
5-alkyl-2-(4'-alkylcarbonyloxyphenyl)pyrimidine,
5-alkoxy-2-(4'-alkylcarbonyloxyphenyl)pyrimidine,
5-alkyl-2-(4'-alkyloxycarbonylphenyl)pyrimidine,
5-alkoxy-2-(4'-alkyloxycarbonylphenyl)pyrimidine,
5-alkyl-2-(4'-alkoxyphenyl)pyrazine,
5-alkoxy-2-(4'-alkoxyphenyl)pyrazine,
5-alkyl-2-(4'-alkylcarbonyloxyphenyl)pyrazine,
5-alkoxy-2-(4'-alkylcarbonyloxyphenyl)pyrazine,
5-alkyl-2-(4'-alkyloxycarbonylphenyl)pyrazine,
5-alkoxy-2-(4'-alkyloxycarbonylphenyl)pyrazine,
3-(4'-alkylphenyl)-6-alkoxypyridazine,
3-(4'-alkoxyphenyl)-6-alkoxypyridazine,
3-(4'-alkoxyphenyl)-6-alkylpyridazine,
5-(4'-alkylphenyl)-2-(4''-alkoxyphenyl)pyrimidine,
5-(4'-alkoxyphenyl)-2-(4''-alkoxyphenyl)pyrimidine,
5-(4'-alkylphenyl)-2-(4''-alkylcarbonyloxyphenyl)pyrimidine,
5-(4'-alkoxyphenyl)-2-(4''-alkylcarbonyloxyphenyl)pyrimidine,
5-(4'-alkylphenyl)-2-(4''-alkyloxycarbonylphenyl)pyrimidine,
5-(4'-alkoxyphenyl)-2-(4''-alkyloxycarbonylphenyl)pyrimidine,
5-(4'-alkoxyphenyl)-2-(4''-alkyloxycarbonylphenyl)pyrimidine,
5-(4'-alkylphenyl)-2-(4''-alkoxyphenylcarbonyloxy)pyrimidine,
5-(4'-alkoxyphenyl)-2-(4''-alkoxyphenylcarbonyloxy)pyrimidine,
5-(4'-alkoxyphenyl)-2-(4''-alkylphenylcarbonyloxy)pyrimidine,
5-(4'-alkylphenyl)-2-(4''-alkylphenylcarbonyloxy)pyrimidine,
5-(4'-alkylphenyl)-2-(4''-alkoxyphenyl)-1,2,4-triazine,
5-(4'-alkoxyphenyl)-2-(4''-alkoxyphenyl)-1,2,4-triazine,
5-(4'-alkylphenyl)-2-(4''-alkylcarbonyloxyphenyl)-1,2,4-triazine,
5-(4'-alkoxyphenyl)-2-(4''-alkylcarbonyloxyphenyl)-1,2,4-triazine,
5-(4'-alkylphenyl)-2-(4''-alkyloxycarbonylphenyl)-1,2,4-triazine and
5-(4'-alkoxyphenyl)-2-(4''-alkyloxycarbonylphenyl)-1,2,4-triazine.

The compound of this invention represented by the general formula (I) is derived as follows;

Some of the compounds represented by the formula (I) are obtained by reacting an active compound of the formula (A)

$$R-X \qquad (A)$$

which is a linear alkyl halide or a linear alcohol tosylate with a hydroxy pyrimidine derivative having a linear alkoxy group represented by the formula (B)

$$R'OH-Ph-Py-OH \qquad (B)$$

wherein R and R' represent a linear alkyl group, X represents a halogen atom or tosyl group in the both formulas (A) and (B). These abbreviations in this paragraph are same in the following formulas (C)–(I).

Some of the phenyl pyrimidine compounds are obtained by reacting an acid halide compound represented by the formula (C)

RCOX  (C)

with a hydroxy pyrimidine derivative having an alkylcarbonyloxy group represented by the formula (D) in a basic solvent.

R'COO—Ph—Py—OH  (D)

Some of the phenyl pyrimidine compounds are obtained by reacting a pyrymidinophenyl derivative having an alkyl group represented by the formula (E)

HO—Ph—Py—OR'  (E)

with a linear alcohol tosylate or a linear alkyl halide in a basic solvent.

Some of the phenyl pyrimidine compounds are obtained by reacting an acid halide compound represented by the formula (C) with a pyrimidine phenyl compound having a linear alkylcarbonyloxy group represented by the formula (E) or (F)

HO—Ph—Py—OCOR'  (F)

Some of the phenyl pyrimidine compounds are obtained by reacting an alkoxyphenylamidine hydrochloric salt represented by the formula (G)

RO—Ph—C(=NH)NH$_2$·HCl  (G)

with an alcoholate compound (H) or an alcoxy malonic acid (I) in a basic solvent, R'O—C(COOC$_2$H$_5$)=CHONa  (H)

R'OCH(COOC$_2$H$_5$)$_2$  (I)

by following reduction of a product after chloronizing of a hydroxy group of the reacting product of a compound (H) and (I).

On the other hand, the compounds represented by the formulas (A)–(I) are obtained easily by following examples.

The phenyl pyrimidine compounds of this invention have a smectic C phase and have a skeleton of a phenyl pyrimidine group. A composition comprising the same has a performance of a high speed response. Since the phenyl pyrimidine compounds are not optically active, the attempts which make to comprising the phenyl pyrimidine compound of this invention in a ferroelectric crystal composition, have been succeeded without limitation of a volume of the comprising compound in the composition and the some properties of the compound such as a helical pitch length or a viscosity. A ferroelectric liquid crystal composition comprising some of the phenyl pyrimidine compound of this invention having a nematic phase within the higher temperature range than that of a smectic phase, has a property to form a nematic phase. And it is able to utilize in practice by using a conventional alignment technique of a TN type cell.

A composition of this invention comprising a phenyl pyrimidine compound forms a smectic C phase within a broad temperature range including room temperature, and has a performance of a high response speed at room temperature, it is able to align the composition by using a conventional technique such as rubbing a polyimide. For example, the compositions described in following examples form a smectic C phase and are a ferroelectric liquid crystal within 1°–70° C. range. And the compositions are able to align easily in an ITO glass cell which is rubbed and coated polyimide. A very clear contrast of the cell was obtained. A response time of the composition needed changing the 90 percentages of a light transparency after applying a rectangular wave of 15 Vp-p/μm was only 112 μs. The phenyl pyrimidine compounds are stable chemically because of having no schiff's base group which a DOBAMBC compound has.

Since a liquid crystal composition comprising the phenyl pyrimidine compound of the present invention is a smectic liquid crystal, the liquid composition can be used for a memory type display element of the heat writing type or laser writing type.

The present invention will now be described in detail with reference to the following examples that by no means limit the scope of the invention.

In the examples, C, SX, S*, Sc*, Sa, N*, N and I phases represent a crystal phase, a smectic phase not clearly identified, a chiral smectic phase not clearly identified, a chiral smectic C phase, a smectic A phase, a chiral nematic phase, a nematic phase and an isotropic phase, respectively.

The compounds of the present invention were purified by silica gel chromatography and recrystallization from an alcohol or hexane. The measured values of the phase transition points, shown hereinafter, will be influenced by the purities of substances.

EXAMPLE 1

Synthesis and evaluation of 2-p-octyloxyphenyl-5-octyloxypyrimidine (A)

C$_8$H$_{17}$—O—Ph—Py—O—C$_8$H$_{17}$  (A)

Benzyloxy acetic acid obtained by reacting benzyl alcohol with chloro acetic acid by Williamson synthesis method was esterized to obtain ethyl benzyloxy acetate (B). 2-benzyloxy-2-ethoxycarbonylethylenolate (C) was obtained by condensing the compound (B) and ethyl formate under the presence of sodium as a catalyzer. Then 2-octyloxyphenyl-4-hydroxy-5-benzyloxypyrimidine (D) was obtained by condensing the compound (C) and p-octyloxybenzamidine hydrochloric salt which was synthesized by using p-octyloxyanobenzene, in an ethanol solvent under the presence of sodium ethoxide. Furthermore, 2-octyloxyphenyl-4-chloro-5-benzyloxypyrimidine (E) was obtained by refluxing reaction of the compound (D) with phosphorus oxychloride for three hours. 2-octyloxyphenyl-5-hydroxypyrimidine (F) was obtained by hydrogenating of the compound (E) under the presence of the both catalyzer Pd-C and potassium carbonate in the 1,4-dioxane solvent under the atmospheric pressure. Finally, the compound (A) was obtained by reacting the compound (F) with octylbromide by Williamson synthesis method.

The phase transition points of the compound (F) were as follows. The figure in ( ) means a phase transition point under lowering temperature.

| | |
|---|---|
| C–S | 52° C. (42° C.) |
| Sc–SA | 91° C. (91° C.) |
| SA–N | 99° C. (99° C.) |
| N–I | 100° C. (100° C.) |

The compound (F) has a nematic phase. The phase transition point of changing from a Sc phase to SA phase of the compound was more than 90° C. The compound (F) is very important as a constituent of a liquid crystal composition.

EXAMPLE 2

Synthesis and evaluation of 2-p-octyloxyphenyl-5-octylcarbonyloxypyrimidine (G)

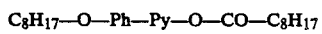

The compound (G) was obtained by reacting the compound (F) with nonanic chloride in pyridine. The phase transition points of the compound were as follows. The figure in ( ) means a phase transition point under lowering temperature.

| | |
|---|---|
| C–Sc | 53° C. (65° C.) |
| Sc–N | 92° C. (91° C.) |
| N–I | 96° C. (96° C.) |

The compound (G) has a nematic phase. The phase transition points of changing from a Sc to a N phase of the compound (G) is more than 90° C. The compound (G) is very important as a constituent of a liquid crystal composition.

EXAMPLE 3

Some of the compounds of this invention obtained by the same method of the example 1 or 2 were shown in the table 1. The lowest temperature forming a Sc phase was very high, 81° C. (cf. The other case was 88° C. without a compound of which the both $R_1$ and $R_2$ are heptyloxy group)

These compound is very important as a constituent of a liquid crystal composition.

COMPARATIVE EXAMPLE 1

The comparative data of a rising temperature range forming a Sc phase between phenylpyrimidine Sc liquid crystal compound of this invention having an alcoxy group and a known phenylpyrimidine Sc liquid crystal compound having an alkyl group were shown in the table 2. As the results, the temperature range of the compound of this invention expanded 20° C. than a known phenylpyrimidine Sc liquid crystal compound having alkyl group. The compound of this invention was very important as a constituent of a liquid crystal composition.

EXAMPLE 4

(Composition 1)

A transition points of a composition (H) obtained by mixing the three different compounds of this invention are as follows. The composition consists of 33.5 wt % of 2-p-octyloxyphenyl-5-octyloxypyrimidine (A), 33.2 wt % of 2-p-decyloxyphenyl-5-octyloxypyrimidine and 33.3 wt % of 2-p-octyloxyphenyl-5-decyloxypyrimidine. The figure in ( ) means a phase transition point under lowering temperature.

| | |
|---|---|
| C–Sc | 32° C. (19° C.) |
| Sc–SA | 93° C. (93° C.) |
| SA–I | 100° C. (100° C.) |

The datum shows that the temperature range forming a Sc phase of the composition (H) expand more than 70° C. under lowering temperature, owing to comprise the compound of this invention.

COMPARATIVE EXAMPLE 2

The phase transition points of a composition (J) comprising the known three phenylpyrimidine liquid crystal compounds having an alkyl group are as follows. The composition consists of 32.9 wt % of 2-p-octylphenyl-5-octyloxypyrimidine, 32.9 wt % of 2-p-nonyloxyphenyl-5-nonylpyrimidine and 34.2 wt % of 2-p-decyloxyphenyl-5-octylpyrimidine. The figure in ( ) means a phase transition point under lowering temperature.

| | |
|---|---|
| C–Sc | 18° C. (9° C.) |
| Sc–SA | 58.5° C. (58.5° C.) |
| SA–N | 68° C. (68° C.) |
| N–I | 70° C. (70° C.) |

The datum shows that a temperature range forming a Sc phase of the composition (J) narrow to 20° C. than that of the example 5 comprising the compound of this invention.

EXAMPLE 5

(Composition 2)

The phase transition points of a composition comprising the three compounds of this invention are as follows. The composition consists of 33.25 wt % of 2-p-octyloxyphenyl-5-octyloxypyrimidine (A), 33.25 wt % of 2-p-decyloxyphenyl-5-octylcarbonyloxypyrimidine and 33.5 wt % of 2-p-octyloxyphenyl-5-octylcarbonyloxypyrimidine. The figure in ( ) means a phase transition point under lowering temperature.

| | |
|---|---|
| C–Sc | 27° C. (17° C.) |
| Sc–SA | 90° C. (90° C.) |
| SA–N | 91° C. (91° C.) |
| N–I | 95° C. (95° C.) |

The temperature range forming a Sc phase expand more than 70° C. under lowering temperature, owing to comprise the compound of this invention. Furthermore, the composition forms a nematic phase.

EXAMPLE 6

(Composition 3)

The phase transition points comprising the two types of the compound of this invention and a known phenylpyrimidine Sc liquid crystal compound having an alkyl group. The composition consists of 33.3 wt % of 2-p-octylphenyl-5-octyloxypyrimidine, 33.4 wt % of 2-p-octyloxyphenyl-5-octyloxypyrimidine (A) and 33.4 wt % of 2-p-octyloxyphenyl-5-octylcarbonyloxypyrimidine. The figure in ( ) means a phase transition point.

| | |
|---|---|
| C–Sc | 36° C. (5° C.) |

| | |
|---|---|
| Sc-SA | 76° C. (76° C.) |
| SA-N | 78° C. (78° C.) |
| N-I | 86° C. (86° C.) |

The results show that a nematic phase range expand more 20° C. than that of the comparative example 2, owing to comprise the compound of this invention. The melting point of the composition (C—Sc phase transition point) lowered.

EXAMPLE 7

(Composition 4)

The phase transition point of a composition comprising the composition (H) described in the composition 1 and a known aromatic ester liquid crystal compounds. The composition consists of 66 wt % of the composition (H), 11.3 wt % of p-octyloxybenzoic acid p-heptyloxyphenyl ester, 11.4 wt % of p-octyloxybenzoic acid p-nonyloxyphenyl ester and 11.3 wt % of p-octyloxybenzoic acid p-hexyloxyphenyl ester. The figure in ( ) means a phase transition point.

| | |
|---|---|
| C-Sc | 23° C. (4° C.) |
| Sc-SA | 78° C. (78° C.) |
| SA-N | 86.5° C. (86.5° C.) |
| N-I | 90° C. (90° C.) |

The melting point of the composition 4 (a C—Sc transition point) lowered. The composition 4 became to form a nematic phase in spite of a no nematic phase of the composition 1 described in the example 4.

EXAMPLE 8

(Composition 5)

The phase transition point of a composition comprising the composition (H) of this invention described in the composition 1 and a known biphenyl ester liquid crystal compound. The composition consists of 89.2 wt % of the composition (H) and 10.8 wt % of p-(p'-octyloxyphenyl) benzoic acid hexylester. The figure in ( ) means a phase transition point under lowering temperature.

| | |
|---|---|
| C-Sc | 28° C. (14° C.) |
| Sc-SA | 85° C. (85° C.) |
| SA-I | 96° C. (96° C.) |

A melting point of the composition 5 (a C—Sc phase transition point) lowered by mixing a known biphenylester Sc liquid crystal compound with the compound of this invention.

EXAMPLE 9

(Composition 6)

A ferroelectric liquid crystal composition (K) having a following phase transition point was obtained by comprising the synthesized novel compound by the inventors. The composition consists of 20.8 wt % of (1S,2S)-4''-4'-octyloxyphenyl)phenyl 1-chloro-2-methylpentanoic acid ester, 11.7 wt % of (1S,2S)-4'''-(4'-nonyloxycarbonyloxyphenyl)phenyl 1-chloro-2-methylpentanoic acid ester, 10.0 wt % of (1S,2S)-4''-(4'-nonylcarbonyloxyphenyl)phenyl 1-chloro-2-methylpentanoic acid ester, 10.0 wt % of (1S)-4'''-(4'-nonylcarbonyloxyphenyl)phenyl 1-chloro-2-methylbutanoic acid ester, 30.5 wt % of (1S,2S)-4'''-(4''-(4'-octylcarbonyloxy-3'-chlorophenylcarbonyloxy)phenyl)phenyl 1-chloro-2-methylpentanoic acid ester and 17.0 wt % of (2S)-p'-(2-methylbutyloxyphenyl)-4-octyloxybenzoic acid ester. A figure in ( ) means a phase transition point under lowering temperature.

| | |
|---|---|
| Sc*-SA | 55° C. (55° C.) |
| SA-N* | 61.5° C. (61.5° C.) |
| N*-I | 65° C. (65° C.) |

The composition showed a ferroelectric liquid crystal phase even to a temperature below 0° C. and a large spontaneous polarization, 183 nC/cm².

The ferroelectric liquid crystal composition (L) was obtained by mixing this composition (K) with the composition (H) described in the composition 1. A ratio of this composition (L) was 1:1. A figure in ( ) means a phase transition point under lowering temperature.

| | |
|---|---|
| Sc*-Sa | 70° C. (70° C.) |
| SA-N* | 76° C. (75.5° C.) |
| N*-I | 79° C. (79° C.) |

The composition showed a ferroelectric liquid crystal phase even to a temperature below 0° C. and a large spontaneous polarization, 85 nC/cm².

The composition having a ferroelectric liquid crystal property within a wide temperature range including a room temperature was obtained by mixing a known compound with the compound of this invention.

The composition was sealed in a cell formed by spin-coating a polyimide on ITO glass and rubbing the coating and having a spacer of a polyethylene terephthalate film having a thickness of 2.5 μm, and the composition was cooled from the isotropic phase at a rate of 0.1° C. per minute, whereby a cell having a good alignment was easily obtained. A rectangular wave of 40 Vp-p was applied to the cell and the electro-optic effect was observed by a polarization microscope. A very clear contrast was seen. It was proved that the composition could be applied to a liquid crystal display. When the response speed of this cell was measured by using a photosemiconductor, it was found that the response speed was required for changing the quantity of transmitted light from 10% to 90% was about 12 microseconds at room temperature, and thus it was confirmed that the response speed was very high.

The ferroelectric liquid crystal composition having an ability of a high speed response was obtained by mixing a known ferroelectric liquid crystal compound or a known compound having a smectic C phase with the compound of this invention.

COMPARATIVE EXAMPLE 3

The ferroelectric liquid crystal compound (K) was mixed with the three types of a known phenylpyrimidine Sc liquid crystal compound having an alkyl group described in the comparative example 1 to obtain the ferroelectric liquid crystal compound (M). The figure in ( ) means a phase transition point under lowering temperature.

| | |
|---|---|
| Sc*-SA | 55° C. (55° C.) |
| SA-N* | 59° C. (58° C.) |

| | |
|---|---|
| N*-I | 62° C. (62° C.) |

The results show that the temperature range of the composition (L) (forming a Sc* phase under lowering temperature) described in the example 9 expand 15° C. than that of the composition described in the comparative example 3. The response speed of the composition (M) was 118 microseconds and it is same as that of the composition (L).

TABLE 1

The phase transition point of
$C_mH_{2m+1}$—X—Ph—Py—Y—$C_nH_{2n+1}$

| m | n | —X— | —Y— | C | SC | SA | N | I |
|---|---|---|---|---|---|---|---|---|
| 7 | 7 | —O— | —O— | • 62 | • 81 | • 88 | • 95 | • |
|   |   |     |     | • 55 | • 81 | • 88 | • 95 | • |
| 7 | 8 | —O— | —O— | • 54 | • 89 | • 97 | • 98 | • |
|   |   |     |     | • 41 | • 89 | • 97 | • 98 | • |
| 7 | 9 | —O— | —O— | • 57 | • 95 | •    | 97   | • |
|   |   |     |     | • 44 | • 95 | •    | 97   | • |
| 8 | 8 | —O— | —O— | • 52 | • 91 | • 99 | • 100 | • |
|   |   |     |     | • 42 | • 91 | • 99 | • 100 | • |
| 8 | 9 | —O— | —O— | • 53 | • 96 | •    | 100  | • |
|   |   |     |     | • 39 | • 96 | •    | 100  | • |
| 8 | 10 | —O— | —O— | • 60 | • 101 | •  | 102  | • |
|   |   |     |     | • 41 | • 101 | •  | 102  | • |
| 9 | 9 | —O— | —O— | • 65 | • 97 | •    | 101  | • |
|   |   |     |     | • 55 | • 97 | •    | 101  | • |
| 10 | 8 | —O— | —O— | • 48 | • 88 | •   | 99   | • |
|    |   |     |     | • 40 | • 88 | •   | 99   | • |
| 10 | 9 | —O— | —O— | • 52 | • 96 | •   | 98   | • |
|    |   |     |     | • 41 | • 96 | •   | 98   | • |
| 10 | 14 | —O— | —O— | • 67 | •    | •   | 103  | • |
|    |   |     |     | • 59 | •    | •   | 103  | • |

The mark —Ph— represents

The mark —Py— represents

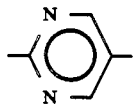

TABLE 1-continued

The phase transition point of
$C_mH_{2m+1}$—X—Ph—Py—Y—$C_nH_{2n+1}$

The upper figures in a column show a temperature under a increasing temperature and the below one show a temperature under a lowering temperature.

| m | n | —X— | —Y— | C | SX | SC | N | I |
|---|---|---|---|---|---|---|---|---|
| 7 | 13 | —O— | —OCO— | • | 81 | • | 101 | • |
|   |    |     |       | • 65 | • 73 | • | 101 | • |
| 8 | 8 | —O— | —OCO— | • | 65 | • 92 | • 96 | • |
|   |   |     |       | • | 53 | • 91 | • 96 | • |
| 8 | 9 | —O— | —OCO— | • | 69 | • | 98 | • |
|   |   |     |       | • | 49 | • | 98 | • |
| 8 | 10 | —O— | —OCO— | • | 75 | • | 100 | • |
|   |    |     |       | • | 53 | • | 100 | • |
| 10 | 8 | —O— | —OCO— | • | 64 | • 93 | • 97 | • |
|    |   |     |       | • | 44 | • 93 | • 97 | • |
| 10 | 9 | —O— | —OCO— | • | 61 | • | 99 | • |
|    |   |     |       | • | 50 | • | 99 | • |
| 10 | 10 | —O— | —OCO— | • | 68 | • | 102 | • |
|    |    |     |       | • | 43 | • | 102 | • |

TABLE 2

The comparison of a temperature range of a Sc phase on the compound *1 of this invention and a known compound *2.

| m | n | —X— | —Y— | Temperature range of a Sc phase of the compound of this [°C.] invention | The temperature range of a Sc phase of a known compound [°C.] |
|---|---|---|---|---|---|
| 7 | 7 | —O— | —O— | 61~79 | no existence of a Sc phase |
| 7 | 8 | —O— | —O— | 54~89 | no existence of a Sc phase |
| 7 | 9 | —O— | —O— | 57~95 | 32.5~48 |
| 8 | 8 | —O— | —O— | 52~91 | 28.5~55.5 |
| 8 | 9 | —O— | —O— | 53~96 | 33~60 |
| 8 | 10 | —O— | —O— | 60~101 | 37~68.5 |
| 10 | 8 | —O— | —O— | 48~88 | 32~59.5 |
| 8 | 8 | —O— | —OCO— | 65~92 | 28.5~55.5 |
| 8 | 9 | —O— | —OCO— | 69~98 | 33~60 |
| 8 | 10 | —O— | —OCO— | 75~100 | 37~68.5 |
| 10 | 8 | —O— | —OCO— | 64~93 | 32~59.5 |
| 10 | 10 | —O— | —OCO— | 68~102 | no existence of a Sc phase |

*1 $C_mH_{2m+1}$—X—Ph—Py—Y—$C_nH_{2m+1}$
*2 $C_mH_{2m+1}$—X—Ph—Py—$C_nH_{2n+1}$
The temperature ranges of a SC phase on the known compound was quoted the figures written in the paper (Flussige Kristalle in Tabellen, Verlag Grundstoffind, Leipzig).

What is claimed is:

1. A smectic C liquid crystal compound represented by the following formula (I)

$$R_1—Ph—Py—R_2 \quad (I)$$

wherein Ph represents 1,4-phenylene group and Py represents 2,5-pyrimidyl group, $R_1$ and $R_2$ represent independently a linear acyloxy group or alkoxy group, either $R_1$ or $R_2$ represents a linear acyloxy group or linear alkoxy group having more than the seven carbon atoms.

2. A smectic C liquid crystal composition comprising at least one phenyl pyrimidine compound represented by the following formula (I):

$$R_1—Ph—Py—R_2 \quad (I)$$

wherein Ph represents a 1,4-phenylene group and Py represents a 2,5-pyrimidyl group, $R_1$ and $R_2$ represent independently, a linear acyloxy group or alkoxy group, either $R_1$ or $R_2$ represents a linear acyloxy group or linear alkoxy group having more than the seven carbon atoms, and at least one other smectic C liquid crystal phenyl pyrimidine.

3. A smectic C liquid crystal composition comprising at least one phenyl pyrimidine compound represented by the following formula (I)

R₁—Ph—Py—R₂     (I)

wherein Ph represents 1,4-phenylene group and Py represents 2,5-pyrimidyl group, R₁ and R₂ represent independently a linear acyloxy group or alkoxy group, either R₁ or R₂ represents a linear acyloxy group or linear alkoxy group having more than the seven carbon atoms, and at least one smectic C liquid crystal ester compound.

4. A smectic C liquid crystal composition comprising at least one phenyl pyrimidine compound represented by the following formula (I)

R₁—Ph—Py—R₂     (I)

wherein Ph represents 1,4-phenylene group and Py represents 2,5-pyrimidyl group, R₁ and R₂ represent independently a linear acyloxy group or alkoxy group, either R₁ or R₂ represents a linear acyloxy group or linear alkoxy group having more than the seven carbon atoms, and at least one smectic C liquid crystal biphenyl compound.

5. The liquid crystal composition as set forth in claim 2, which has a nematic phase.

6. The liquid crystal composition as set forth in claim 3, which has a nematic phase.

7. The liquid crystal composition as set forth in claim 4, which has a nematic phase.

8. The chiral smectic C liquid crystal composition comprising a smectic C liquid crystal composition as set forth in claim 2, which further comprises at least one optically active compound.

9. The chiral smectic C liquid crystal composition comprising a smectic C liquid crystal composition as set forth in claim 3, which further comprises at least one optically active compound.

10. The chiral smectic C liquid crystal composition comprising a smectic C liquid crystal composition as set forth in claim 4, which further comprises at least one optically active compound.

11. A smectic C phenyl pyrimidine compound of formula (I)

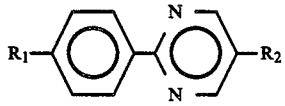

wherein R₁ is a linear alkoxy of more than seven carbon atoms and group R₂ is a linear acyloxy or linear alkoxy group having more than seven carbons.

* * * * *